(12) United States Patent
Mulholland et al.

(10) Patent No.: US 7,232,902 B2
(45) Date of Patent: Jun. 19, 2007

(54) PROCESS TO PREPARE (1-CARBOXYMETHYL)-PYRIMIDINONE COMPOUNDS

(75) Inventors: Keith Raymond Mulholland, Harlow (GB); Andrew R Ross, Irvine (GB); Graham Ralph Slater, Stevenage (GB); Gillian Elizabeth Smith, Tonbridge (GB)

(73) Assignee: SmithKline Beecham p.l.c. (GB)

( * ) Notice: Subject to any disclaimer, the term of this patent is extended or adjusted under 35 U.S.C. 154(b) by 460 days.

(21) Appl. No.: 10/485,972

(22) PCT Filed: Aug. 13, 2002

(86) PCT No.: PCT/EP02/09067

§ 371 (c)(1),
(2), (4) Date: Jul. 2, 2004

(87) PCT Pub. No.: WO03/016287

PCT Pub. Date: Feb. 27, 2003

(65) Prior Publication Data

US 2004/0242875 A1    Dec. 2, 2004

(30) Foreign Application Priority Data

Aug. 14, 2001 (GB) ................. 0119795.3

(51) Int. Cl.
*C07D 239/56* (2006.01)
(52) U.S. Cl. .............. 544/253; 544/285; 544/309
(58) Field of Classification Search ............... 544/253, 544/285, 309
See application file for complete search history.

(56) References Cited

FOREIGN PATENT DOCUMENTS

WO     WO 01/60805     8/2001

OTHER PUBLICATIONS

Lempert et al., "rH-3, 1-Benzoxazin-4-one. I. Rearrangement of N-(2-carboxyphenyl)cyanamide and N-(2-carboxyphenyl)carbodiimides into 1,2-dihydro-2-imino-4H-3, 1-benzoxazin-4-one and 1,2,3,4-tetrahydroquinazoline-2, 4-dione", Monatsh, 1964, 95(3), pp. 950-960.

*Primary Examiner*—Deepak Rao
(74) *Attorney, Agent, or Firm*—James M. Kanagy; Mary McCarthy; Charles Kinzig

(57) ABSTRACT

The invention relates to a process for the preparation of certain pyrimidinone compounds.

12 Claims, No Drawings

PROCESS TO PREPARE (1-CARBOXYMETHYL)-PYRIMIDINONE COMPOUNDS

This is a §371 national stage filing of PCT/EP02/09067 filed 13 Aug. 2002.

The present invention relates to a process for the preparation of certain pyrimidinone compounds.

WO 01/60805 (SmithKline Beecham plc), unpublished at the priority date of the instant application, discloses a novel class of pyrimidinone compounds, inter alia those substituted at N1.

The pyrimidinone compounds described in WO 01/60805 are inhibitors of the enzyme lipoprotein associated phospholipase $A_2$ (Lp-PLA$_2$) and as such are expected to be of use in therapy, in particular in the primary and secondary prevention of acute coronary events, for instance those caused by atherosclerosis, including peripheral vascular atherosclerosis and cerebrovascular atherosclerosis.

Several processes for the preparation of such pyrimidinone compounds are also disclosed in WO 01/60805, inter alia alkylation of the pyrimidinone nucleus. This process generally suffers from moderate yields due to the poor selectivity seen in the alkylation of the pyrimidinone nucleus.

The present invention provides particularly advantageous processes, not hitherto disclosed, for both the preparation of the pyrimidinone compounds disclosed in WO 01/60805 and the preparation of a key intermediate for use in the synthesis of such compounds.

Accordingly, in a first aspect the instant invention provides a process for preparing a compound of formula (I):

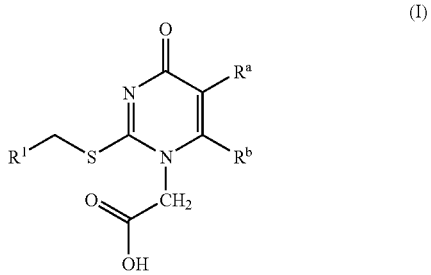

(I)

wherein:
  $R^a$ and $R^b$ together are $(CH_2)_n$ where n is 3 or 4, to form, with the pyrimidine ring carbon atoms to which they are attached, a fused 5- or 6-membered carbocyclic ring; and
  $R^1$ is phenyl optionally substituted by halogen; which comprises:
(a) reacting a compound of formula (II)

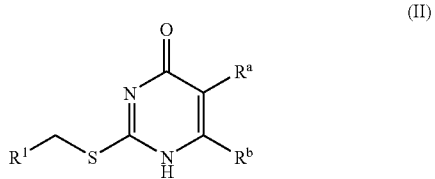

(II)

wherein $R^1$, $R^a$ and $R^b$ are as defined for formula (I), or a protected derivative thereof, with a silylating agent in an inert organic solvent, in the presence of a non-aqueous catalyst;
(b) treating the product from step (a) above with (trifluoromethanesulfonyloxy)-acetic acid methyl ester in an inert organic solvent; and
(c) basic hydrolysis of the methyl ester resulting from step (b).

The process according to the invention is particularly advantageous as it results in selective N1-alkylation of the pyrimidinone nucleus and allows synthesis of the compound of formula (I) without the need to isolate the intermediate ester. Hence, the process is both high yielding and efficient.

In a further aspect the silylating agent is 1,1,1,3,3,3-hexamethyldisilazane.

In a further aspect the non-aqueous catalyst is saccharin.

In a further aspect the inert organic solvent is dichloromethane.

In a further aspect the basic hydrolysis of step (c) is performed in an alcoholic solvent. Preferably the alcoholic solvent is isopropyl alcohol.

In a further aspect the hydrolysis step (c) is achieved using aqueous sodium hydroxide.

In a further aspect steps (a) and (b) are carried out between ambient temperature and reflux. Conveniently the temperature is from 20° C. to about 60° C., preferably 35° C. to 45° C.

In a further aspect the invention provides a process for the preparation of a pyrimidinone compound of formula (I) wherein $R^a$ and $R^b$, together with the pyrimidine ring atoms to which they are attached, form a fused 5-membered carbocyclic ring.

In a further aspect the invention provides a process for the preparation of a pyrimidinone compound of formula (I) wherein $R^1$ is phenyl optionally substituted by one to three fluorine atoms, preferably 4-fluoro.

In a further aspect the invention provides a process for the preparation of 1-(carboxymethyl)-2-(4-fluorobenzylthio)-5,6-trimethylenepyrimidin-4-one.

In a further aspect the invention provides compounds of formula (I).

Compounds of formula (II) for use in the above process may be prepared according to Scheme 1 below.

Scheme 1

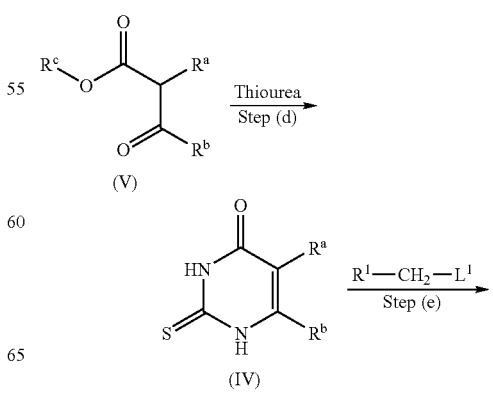

-continued

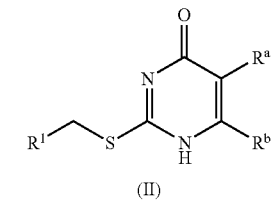
(II)

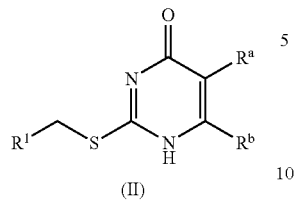
(III)

With reference to Scheme 1:

$R^c$ is $C_{1-4}$alkyl, such as methyl. Compounds of formula (V) are known compounds or may be prepared in a conventional manner.

Compounds of formula (IV) may be prepared from compounds of formula (V), according to step (d), via treatment with thiourea in the presence of a base such as sodium ethoxide. Step (d) may be advantageously carried out in refluxing acetonitrile in the presence of 1,8-diazabicyclo[5.4.0]undec-7-ene (DBU), or in refluxing 1,2-dimethoxyethane (DME). Alternatively, step (d) may be advantageously carried out in refluxing toluene/diglyme in the presence of piperidine.

Compounds of formula (II) may be prepared from compounds of formula (IV) according to step (e) wherein $R^1$ is as hereinbefore described and $L^1$ is a leaving group such as halogen, for instance chloro, bromo or iodo, or triflate. Advantageously, the reaction is carried out in the presence of a base such as sodium ethoxide or potassium carbonate, preferably in a solvent such as ethanol, dimethyl formamide or acetone, or in the presence of a secondary or tertiary amine base such as di-isopropylethylamine, in a solvent such as dichloromethane. Alternatively, step (e) may be advantageously performed in the presence of sodium hydroxide in a mixture of 2-propanol and water where $L^1$ is chloro.

The intermediates of formula (I) may be transformed into final compounds of formula (III) via amide forming reactions, as described in WO 01/60805. Such amide forming reactions are well known in the art, see for instance Comprehensive Organic Synthesis 6, 382-399, and include reacting an acid compound and an amine compound in an inert solvent, at ambient temperature, in the presence of a coupling agent. WO 01/60805 describes the use of 1-(3-dimethylaminopropyl)-3-ethylcarbodiimide hydrochloride (EDC), preferably in the presence of an additive such as 1-hydroxybenzotriazole, or O-(7-azabenzotriazol-1-yl)-N,N,N',N'-tetramethyluronium hexafluorophosphate (HATU), preferably in the presence of diisopropylamine, as coupling agents.

We have now found a superior coupling agent, not hitherto disclosed.

Accordingly, in a further aspect the invention provides a process for the preparation of a pyrimidinone compound of formula (III)

wherein:

$R^a$ and $R^b$ together with the pyrimidine ring carbon atoms to which they are attached form a fused 5-membered carbocyclic ring;

$R^1$ is 4-fluorophenyl;

$R^2$ is $C_{(1-3)}$alkyl substituted by $NR^5R^6$; or $R^2$ is Het-$C_{(0-2)}$alkyl in which Het is a 5- to 7-membered heterocyclyl ring containing N and in which N may be substituted by $C_{(1-6)}$alkyl;

$R^3$ and $R^4$ form a 4-(4-trifluoromethylphenyl)phenyl moiety; and $R^5$ and $R^6$ which may be the same or different is each selected from hydrogen, or $C_{(1-6)}$alkyl; which comprises:

a) reacting a compound of formula (I), wherein $R^1$, $R^a$ and $R^b$ are as defined for formula (III), or a protected derivative thereof, with an amine of formula (VI)

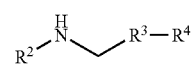
(VI)

wherein $R^2$, $R^3$ and $R^4$ are as defined for formula (III), in an inert organic solvent in the presence of O-benzotriazole-1-yl-N,N,N',N'-tetramethyluronium tetrafluoroborate (TBTU) and an amine base.

The process according to the invention is particularly advantageous as it affords the required product in both high yield and purity.

In a further aspect the inert organic solvent is dichloromethane.

In a further aspect the amine base is di-isopropylethylamine.

In a further aspect the invention provides a process for the preparation of 1-(N-(2-(diethylamino)ethyl)-N-(4-(4-trifluoromethylphenyl)benzyl)-aminocarbonylmethyl)-2-(4-fluorobenzyl)thio-5,6-trimethylenepyrimidin-4-one, a compound of formula (III).

In a further aspect the invention provides a process for the preparation of a compound of formula (III) which comprises the steps of:

(a) reacting a compound of formula (II)

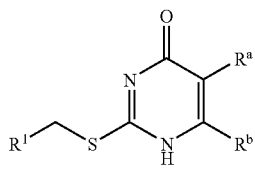

wherein $R^1$, $R^a$ and $R^b$ are as defined for formula (III), or a protected derivative thereof, with a silylating agent in an inert organic solvent, in the presence of a non-aqueous catalyst;
(b) treating the product from step (a) above with (trifluoromethanesulfonyloxy)-acetic acid methyl ester in an inert organic solvent; and
(c) basic hydrolysis of the methyl ester resulting from step (b).

In a further aspect the invention provides a process for the preparation of a compound of formula (III) which comprises:
(a) reacting a compound of formula (II)

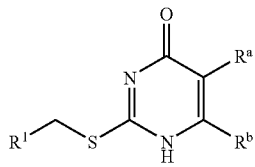

wherein $R^1$, $R^a$ and $R^b$ are as defined for formula (III), or a protected derivative thereof, with a silylating agent in an inert organic solvent, in the presence of a non-aqueous catalyst;
(b) treating the product from step (a) above with (trifluoromethanesulfonyloxy)-acetic acid methyl ester in an inert organic solvent;
(c) basic hydrolysis of the methyl ester resulting from step (b); and
(d) reacting a compound of formula (I) resulting from step (c) above, wherein $R^1$, $R^a$ and $R^b$ are as defined for formula (III), or a protected derivative thereof, with an amine of formula (VI)

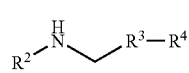

wherein $R^2$, $R^3$ and $R^4$ are as defined for formula (III), in an inert organic solvent in the presence of O-benzotriazole-1-yl-N,N,N',N'-tetramethyluronium tetrafluoroborate (TBTU) and an amine base.

Compounds of formula (VI) for use in the above process may be prepared by literature methods such as those described in WO 00/66567 (SmithKline Beecham plc); incorporated herein by reference.

When used herein, the term "halogen" includes fluorine, chlorine, bromine and iodine.

As will be appreciated by those skilled in the art it may be necessary or desirable at any stage in the synthesis of compounds of formula (I) or (III) to protect one or more sensitive groups in the molecule so as to prevent unwanted side reactions.

The protecting groups used in the preparation of compounds of formula (I) and (III) may be used in a conventional manner. See for example, those described in "Protective Groups in Organic Synthesis" by Theodora W. Green and Peter G. M. Wuts, second edition (John Wiley and Sons, 1991) incorporated herein by reference, which also describes methods for the removal of such groups.

Different crystallisation conditions may lead to the formation of different polymorphic forms of crystalline products. This invention includes within its scope all novel processes for preparing the polymorphic forms of the compounds of formula (III) and all novel polymorphs thereby obtained.

The following Examples illustrate, but do not in any way limit, the invention. The following abbreviations are used: DCM, dichloromethane; HMDS, 1,1,1,3,3,3-hexamethyldisilazane; IPA, isopropyl alcohol; TBTU, O-benzotriazole-1-yl-N,N,N',N'-tetramethyluronium tetrafluoroborate.

EXAMPLE 1

1-(Carboxymethyl)-2-(4-fluorobenzylthio)-5,6-trimethylenepyrimidin-4-one

Route A i) 5,6-Trimethylene-2-thiouracil

Thiourea (14.47 kg, 188.24 moles) was stirred in acetonitrile (298 L) and ethyl 2-oxocyclopentanecarboxylate (20.02 kg, 125.62 moles) was added to the mixture and washed in with acetonitrile (24 L). 1,8-diazobicyclo[5.4.0]undec-7-ene (23.40 kg, 150.63 moles) was added, washed in with acetonitrile (24 L) and the resultant solution heated at 59-82° C. for 19.5 hours. After cooling to 3° C. the acetonitrile was decanted off, process water (295 L) was added and the pH adjusted to 1 with concentrated hydrochloric acid (13.3 kg, 131.18 moles) which was rinsed in with process water (19 L). The mixture was stirred at 17° C. for 30 minutes then the solid collected in a centrifuge, washed with water (252 L) then dried at 42° C. for ca. 24 hours, to give the title compound (14.31 kg, 67.6%) as a white solid. $^1$H NMR ($d_6$ DMSO) δ 1.95 (2H, m), 2.50 (2H, t), 2.70 (2H, t), 12.20 (1H, s), 12.6 (1H, s)

ii) 2-(4-Fluorobenzylthio)-5,6-trimethylenepyrimidin-4-one 5,6-Trimethylene-2-thiouracil (4.75 kg, 40.01 moles), potassium carbonate (7.58 kg at 100%, 54.81 moles) and potassium iodide (0.66 kg, 4.00 moles) were stirred in acetone (128 L). 4-Fluorobenzyl chloride (6.15 kg, 42.11 moles) was added and rinsed in with acetone (7 L). The mixture was heated to reflux (ca. 54° C.) for 1 hour then further potassium carbonate (1.00 kg at 100%, 7.23 moles) was added. Reflux was continued for a further 2 hours at which time the reaction was shown to be complete by HPLC. After cooling to 18° C., process water (61 L) was added and the pH of the solution adjusted to 2 with the addition of concentrated hydrochloric acid (5.58 kg, 55.04 moles) which was rinsed in with process water (7 L). The reactor walls were rinsed with process water (7 L) and the slurry stirred at 25° C. for 30 minutes. The pH was readjusted to 2 with the addition of concentrated hydrochloric acid (4.0 kg, 39.45 moles). The resultant slurry was stirred for 10 minutes then the solid was collected by filtration, washed with water (2×68 L) and dried at 45-55° C. for 41.5 hours, to give the title compound (9.80 kg, 86.5%) as a white solid. $^1$H NMR (d$_6$ DMSO) δ 1.95 (2H, m), 2.60 (2H, t), 2.78 (2H, t), 4.38 (2H, s), 7.12 (2H, t), 7.44 (2H, t), 12.50 (1H, s).

iii) 1-(Carboxymethyl)-2-(4-fluorobenzylthio)-5,6-trimethylenepyrimidin-4-one A flask was charged with 2-(4-fluorobenzylthio)-5,6-trimethylenepyrimidin-4-one (50 g) and saccharin (0.5 g). DCM (250 ml) was then added the suspension was then warmed to reflux. Hexamethyldisilazane (HMDS) (22.8 ml.) was added slowly and stirred for 1 hr 30 min. (Trifluoromethanesulfonyloxy)-acetic acid methyl ester solution (approx. 68 g, 1.5 eq. in DCM 50 ml) was then added portion wise over 10 mins. Residual (trifluoromethanesulfonyloxy)-acetic acid methyl ester was then washed-in with DCM (10 ml). The solution was then refluxed for 10 hrs. The golden brown solution was then added, over 25 mins, to a flask containing IPA (500 ml) and a solution of 10%(w/v) NaOH (250 ml). After a further 35 mins stirring the solution was analysed by HPLC and then water (375 ml) was added. The 2-phase mixture was allowed to separate and the organic layer extracted with a solution of 10% NaOH (250 ml). The residual DCM/IPA was removed in vacuo from the combined aqueous layers before cooling to between 20-25° C. The pH was then adjusted, using 5M HCl (approx. 200 ml), to pH 1-3 over 15 min, keeping the temperature between 20-25° C. The solids, thus formed, were removed by filtration and washed with 2×H$_2$O (100 ml) and then 2×toluene (100 ml) and dried in vacuo at 40° C. to yield the title compound as an off white solid 41.8 g (69%). $^1$H NMR (d$_6$ DMSO) δ 1.95 (2H, m), 2.57 (2H, t), 2.85 (2H, t), 4.4 (2H, s), 4.7 (2H, s), 7.15 (2H, dd), 7.45 (2H, dd), ~13.6 (1H, vbrs).

Route B i) 5.6-Trimethylene-2-thiouracil

A mixture of ethyl 2-oxocyclopentanecarboxylate (350 g, 2.24 moles), thiourea (162 g@99%, 160.4 g, 2.11 mole), and piperidine (210 g@99%, 207.9 g, 2.44 moles) in toluene (3.15 L) was stirred and heated to reflux for 1.5 hours with azeotropic removal of water (ca. 0.06 vols removed), then a portion of the solvent (875 ml) was removed by distillation over 1.5 hours. The mixture was cooled to 80° C. and diglyme (1.23 L) added. The resulting mixture was heated back to reflux (in-pot temperature ca. 120° C.) for 24 hours with azeotropic removal of water (ca. 0.1 vols removed). The mixture was cooled to ambient temperature and treated with concentrated hydrochloric acid (350 ml, 1 vol) in water (3.5 L, 10 vols) The resultant mixture was stirred for 4 hours, then filtered and the isolated solid washed with water (2.8 L). The resultant solid wet cake was dried in vacuo at 45° C. to give the title compound (319 g, 90%) as a pale pink solid. $^1$H NMR (d$_6$ DMSO) δ 1.95 (2H, m), 2.50 (2H, t), 2.70 (2H, t), 12.20 (1H, s), 12.6 (1H, s)

ii) 2-(4-Fluorobenzylthio)-5,6-trimethylenepyrimidin-4-one

A suspension of 5,6-trimethylene-2-thiouracil (206.11 g, 1.225 moles) in water (2.89 L) and isopropanol (1.03 L) was warmed to 34-38° C. with stirring. To the suspension was added sodium hydroxide (32% w/w aq NaOH) (175.2 g, 1.40 moles) and the resultant solution stirred for 1 hour at 34-38° C. A solution of 4-fluorobenzyl chloride (179.3 g, 1.24 moles) in isopropanol (824 ml) was added with stirring at 34-38° C. over 20 minutes and washed in with isopropanol (206 ml). The resulting mixture was stirred at 34-38° C. for 2.5 hours, then the suspension was cooled to 15-20° and dilute aqueous hydrochloric acid (0.5M, 412 ml) was added. The resulting suspension was stirred for 20 minutes, and then filtered. The isolated solid was washed with water (2×620 ml) and dried at 40° C., under vacuum to give the title compound (329.1 g, 97%) as a white solid. $^1$H NMR (d$_6$ DMSO) δ 1.95 (2H, m), 2.60 (2H, t), 2.78 (2H, t), 4.38 (2H, s), 7.12 (2H,t), 7.44 (2H, t), 12.50 (1H, s).

iii) 1-(Carboxymethyl)-2-4-fluorobenzylthio)-5,6-trimethylenepyrimidin-4-one As for step (iii) Route A above.

EXAMPLE 2

1-(N-(2-(Diethylamino)ethyl)-N-4-(4-trifluoromethylphenyl)benzyl)-aminocarbonylmethyl)-2-(4-fluorobenzyl)thio-5,6-trimethylenepyrimidin-4-one (Form 2)

i) 4-(4-Trifluoromethylphenyl)benzaldehyde

5% Palladium on carbon, type 58, 50% paste (0.94 kg, 0.22 moles Pd) was added to a mixture of 4-bromobenzaldehyde (3.34 kg, 17.69 moles), 4-trifluoromethylphenyl boronic acid (3.50 kg, 18.06 moles) and sodium carbonate (3.75 kg, 35.38 moles) in process water (36 L). Isopropanol (36 L) was added and the resultant mixture heated to reflux (80-83° C.) for ca. 2.5 hours. The catalyst was removed from the hot suspension by filtration through celite (1.5 kg). The celite bed was washed with a hot (ca. 70° C.) isopropanol (10 L)/water (10 L) mixture then the combined filtrate and wash were cooled to 23° C., process water (18 L) was added and the mixture stirred at 20-25° C. for ca. 17.5 hours. The solid was collected by filtration, washed with process water (1×27 L, 2×18 L) then dried at 39° C. for 24 hours to give the title compound (3.78 kg, 85%) as a white solid. $^1$H NMR (CDCl$_3$) δ 7.75 (4H, s), 7.78 (2H, d) 7.98 (2H, d), 10.10 (1H, s)

ii) N-(2-(Diethylamino)ethyl)-4-(4-trifluoromethylphenyl)benzylamine

N,N-diethylethylene diamine (2.50 kg, 21.12 moles) was added to a solution of 4-(4-trifluoromethylphenyl)benzaldehyde (3.54 kg, 14.08 moles) in toluene (21 L) and rinsed in with toluene (14 L) with stirring. The resultant solution was stirred at 17-21° C. for ca. 96 hours. The solution was then transferred to a hydrogenation vessel containing 5% palladium on alumina (0.213 kg, 0.11 moles Pd) and rinsed in with toluene (37 L). The mixture was hydrogenated at 19–27° C., 50 psig hydrogen for 1 hour until no further hydrogen was consumed. The catalyst was removed by filtration through celite (0.5 kg) and the celite bed was washed with toluene (14 L). The combined filtrate and wash were washed with process water (3×14 L) then the toluene removed by distillation at 20-80° C. in vacuo to give the title compound as a pale yellow oil (4.96 kg, 97.3%). $^1$H NMR (CDCl$_3$) δ 1.01 (6H, t), 2.52 (4H, q), 2.58 (2H, t), 2.70 (2H, t),3.86 (2H, s), 7.42 (2H, d), 7.43 (2H, d), 7.68 (4H, s).

iii) 1-(N-(2-(Diethylamino)ethyl)-N-(4-(4-trifluoromethylphenyl)benzyl)-aminocarbonylmethyl)-2-(4-fluorobenzyl)thio-5,6-trimethylenepyrimidin-4-one (Form 2)

A suspension of 1-(carboxymethyl)-2-(4-fluorobenzylthio)-5,6-trimethylenepyrimidin-4-one (15.00 g, 0.0447 moles) in dichloromethane (175 ml), was treated with N,N-diisopropylethylamine (8.20 ml, 0.0469 mmol) followed by a solution N-(2-(diethylamino)ethyl)-4-(4-trifluoromethylphenyl)benzylamine (15.09 g, 0.0426 moles) in dichloromethane (25 ml). O-Benzotriazole-1-yl-N,N,N',N'-tetramethyluronium tetrafluoroborate (TBTU) (15.05 g, 0.0469 mmol) was then added followed by DCM (25 ml)-rinse of addition funnel. The resultant mixture was stirred at 20-29° C. for 4 hours until complete reaction was seen by HPLC. The reaction mixture was then washed with water (225 ml), 5% sodium carbonate solution (225 ml) and water (225 ml). The organic layer was heated to reflux (38-39° C.) and ca. 75 ml of distillate collected. Methanol (150 ml) was charged and the distillation continued (41-60° C.) until a total of ca. 225 ml was collected. Methanol (125 ml) was added and distillation continued (60-64° C.) until a total of ca. 325 ml was collected. The solution was cooled to 5° C. and stirred at 1-5° C. for 1 hour. The crude product was filtered, washed with chilled methanol (3×40 ml) at ca. 5° C. and dried in vacuo at 45° C. for ca. 21 hours to give the crude title compound (Form 2) as white solid (26.24 g). ν max (Nujol) 3662, 3392, 1660, 1633, 1617, 1609, 1564, 1509, 1487, 1426, 1325, 1220, 1200, 1158, 1118, 1070, 1025, 1015, 1005, 987, 962, 951, 868, 844, 824, 778, 759, 747, 613, 568, 485 cm$^{-1}$.

EXAMPLE 3

1-(N-(2-Diethylamino)ethyl)-N-(4-(4-trifluoromethylphenyl)benzyl)-aminocarbonylmethyl-2-(4-fluorobenzylthio-5,6-trimethylenepyrimidin-4-one (Form 1)

The product from Example 2 (Form 2) (26.0 g, 0.0367 moles) was stirred in isopropyl acetate (156 ml) and heated to reflux (88° C.) The resultant solution allowed to cool to 86° C. and was filtered under vacuum through a sintered funnel. The sintered funnel was then washed with isopropyl acetate (13 ml). The filtrate was then heated to reflux and distilled at atmospheric pressure until 65 ml of distillate had been collected. The solution was then allowed to cool to 25° C. and was seeded with the title compound (Form 1) (0.050 g). The solution was stirred at 21-22° C. for ca. 20 hours during which time crystallisation occurred. The resultant suspension was then filtered, washed with isopropyl acetate (3×30 ml) and dried in vacuo at 45° C. for 23 hours to give the title compound (Form 1) (24.92 g, 88%) as a white solid. $^1$H NMR (CDCl$_3$, ca 1.9:1 rotamer mixture) δ 0.99 (6H, t), 2.10 (2H, m), 2.50 (4H, q), 2.58/2.62 (2H, 2×t), 2.70/2.82 (2H, 2×t), 2.86 (2H, t), 3.28/3.58 (2H, 2×t), 4.45/4.52 (2H, 2×s), 4.68/4.70 (2H, 2 x s), 4.93 (2H, s), 6.95 (2H, m), 7.31 (2H, d), 7.31/7.37 (21, 2×m), 7.48/7.52 (2H, d), 7.65 (2H, m), 7.72 (2H, m); MS (APCI) (M+H)$^+$667; mp 125° C. (by DSC—asymmetric endotherm). ν max (Nujol) 1657, 1636, 1615, 1511, 1493, 1421, 1399, 1327, 1280, 1233, 1195, 1182, 1166, 1156, 1109, 1069, 1017, 1006, 988, 965, 861, 846, 833, 777, 759, 735, 667, 643, 600, 570, 550, 526, 487 cm$^{-1}$.

EXAMPLE 4

Recrystallisation of 1N-(2-(diethylamino)ethyl-N-(4-(4-trifluoromethylphenyl)benzyl)-aminocarbonylmethyl)-2-(4-fluorobenzyl)thio-5,6-trimethylenepyrimidin-4-one (Form 1).

1-(N-(2-(Diethylamino)ethyl)-N-(4-(4-trifluoromethylphenyl)benzyl)-aminocarbonylmethyl)-2-(4-fluorobenzyl)thio-5,6-trimethylenepyrimidin-4-one (Form 1) (260.02 g, 0.390 moles) prepared according to Example 3(a) WO 01/60805 was suspended in isopropyl acetate (900 mL) and the stirred suspension was heated until a solution was attained (75° C.). The mixture was cooled to ambient temperature and stirred for 18 hours. The resulting slurry was filtered and the isolated solid washed with isopropyl acetate (3×100 ml). The solid was dried on the filter bed for 20 minutes and then under reduced pressure (5 mmHg) at 35° C. for 46 hours. The dried solid was passed through a 500 micron sieve to remove lumps to give the title compound (Form 1) as a pale yellow solid (246.26 g, 94.7%). $^1$H NMR (CDCl$_3$, ca 1.9:1 rotamer mixture) δ 0.99 (6H, t), 2.10 (2H, m), 2.50 (4H, q), 2.58/2.62 (2H, 2×t), 2.70/2.82 (2H, 2×t), 2.86 (2H, 2×t), 4.45/4.52 (2H, 2×s), 4.68/4.70 (2H, 2×s), 4.93 (2H, s), 6.95 (2H, m), 7.31/7.37 (2H, 2×m), 7.48/7.52 (2H, d), 7.65 (2H, m), 7.72 (2H, m); MS (APCI) (M+H)$^+$667; mp 126° C. (by DSC—asymmetric endotherm).

We believe that 1-(N-(2-(diethylamino)ethyl)-N-(4-(4-trifluoromethylphenyl)benzyl)-aminocarbonylmethyl)-2-(4-fluorobenzyl)thio-5,6-trimethylenepyrimidin-4-one (Form 1) is more thermodynamically stable than 1-(N-(2-diethylamino)ethyl)-N-(4-(4-trifluoromethylphenyl)benzyl)-aminocarbonylmethyl)-2-(4-fluorobenzyl)thio-5,6-triethylenepyrimidin-4-one (Form 2).

The invention claimed is:

1. A process for preparing a compound of formula (I):

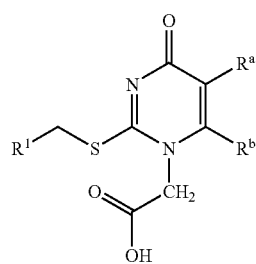

(I)

wherein:

$R^a$ and $R^b$ together are $(CH_2)_n$ where n is 3 or 4, to form, with the pyrimidine ring carbon atoms to which they are attached, a fused 5- or 6-membered carbocyclic ring;

$R^1$ is phenyl optionally susbstituted by halogen;

which comprises:

(a) reacting a compound of formula (II)

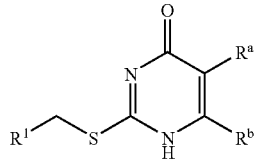

wherein $R^1$, $R^a$ and $R^b$ are as defined for formula (I), or a protected derivative thereof, with a silylating agent in an inert organic solvent, in the presence of a non-aqueous catalyst;

(b) treating the product from step (a) above with (trifluoromethanesulfonyloxy)-acetic acid methyl ester in an inert organic solvent; and (c) basic hydrolysis of the methyl ester resulting from step (b).

2. A process as claimed in claim 1 wherein the silylating agent is 1,1,1,3,3,3-hexamethyldisilazane.

3. A process as claimed in claim 1 wherein the non-aqueous catalyst is saccharin.

4. A process as claimed in claim 1 wherein the inert organic solvent is dichloromethane.

5. A process as claimed in claim 1 wherein the basic hydrolysis of step (c) is performed in an alcoholic solvent.

6. A process as claimed in claim 5 wherein the alcoholic solvent is isopropyl alcohol.

7. A process as claimed in claim 1 wherein step (c) is achieved using aqueous sodium hydroxide.

8. A process as claimed in claim 1 wherein steps (a) and (b) are carried out between ambient temperature and reflux.

9. A process according to claim 1 for the preparation of a compound of formula (I) wherein $R^a$ and $R^b$, together with the pyrimidine ring atoms to which they are attached, form a fused 5-membered carbocyclic ring.

10. A process according to claim 1 for the preparation of a compound of formula (I) wherein $R^1$ is phenyl optionally substituted by one to three fluorine atoms.

11. A process according to claim 10 for the preparation of a compound of formula (I) wherein $R^1$ is 4-fluorophenyl.

12. A process according to claim 1 for the preparation of 1-(carboxymethyl)-2-(4-fluorobenzylthio)-5,6-trimethylenepyrimidin-4-one.

* * * * *